United States Patent [19]

Yoshikumi et al.

[11] 4,237,233

[45] Dec. 2, 1980

[54] METHOD FOR CULTIVATING BASIDIOMYCETES

[75] Inventors: Chikao Yoshikumi, Kunitachi; Toshihiko Wada, Mibu; Hiromitsu Makita, Tokyo; Kinzaburo Suzuki, Mibu; Azuma Okubo, Mibu; Takishi Nakanoya, Mibu; Katsunori Miura, Mibu; Tadao Sagi, Mibu, all of Japan

[73] Assignee: Kureha Kagaku Kogyo Kabushiki Kaisha, Tokyo, Japan

[21] Appl. No.: 819,401

[22] Filed: Jul. 26, 1977

[30] Foreign Application Priority Data

Aug. 3, 1976 [JP] Japan ................................ 51-93074
Aug. 30, 1976 [JP] Japan ............................... 51-103380

[51] Int. Cl.$^3$ ............................................. C12N 1/14
[52] U.S. Cl. ...................................... 435/254; 435/812
[58] Field of Search ................ 195/81, 107, 109, 117; 435/101, 254, 812

[56] References Cited

U.S. PATENT DOCUMENTS

| | | | |
|---|---|---|---|
| 3,672,953 | 6/1972 | Coty et al. | 195/107 |
| 3,780,069 | 12/1973 | Umezawa et al. | 195/51 R |
| 4,051,314 | 9/1977 | Ohtsuka et al. | 195/31 P |

OTHER PUBLICATIONS

Szarka et al., "Foams of fermentation broths. I. Parameters of the foaming of fermentation media", *Chem. Abstracts*, vol. 72, No. 3, (1970) pp. 205 abs No. 11345cl.

*Primary Examiner*—Thomas G. Wiseman
*Attorney, Agent, or Firm*—Stevens, Davis, Miller & Mosher

[57] ABSTRACT

In cultivation of the Basidiomycetes under aeration and agitation in an aqueous liquid medium containing saccharide as a carbon source and yeast extract, peptone, casamino acid and/or meat extract as nutrient, the initial charge of the medium is adjusted such that it is less than about 70% of the capacity of the fermentor used, and the medium or at least one component thereof is supplied additionally in portions as cultivation advances. Such control of the medium feed suppresses excessive foaming which occurs in the aqueous medium during cultivation, and allows smooth and efficient cultivation of the Basidiomycetes.

7 Claims, No Drawings

METHOD FOR CULTIVATING BASIDIOMYCETES

BACKGROUND OF THE INVENTION

This invention relates to a method of cultivating Basidiomycetes at high efficiency, while controlling occurence of excessive foaming, under aeration and agitation by using an aqueous liquid medium which produces vigorous foaming during cultivation of the fungi.

Generally, the aqueous liquid media of the type containing at least one substance selected from yeast extract, peptone, casamino acid and meat extract as a nutrient source (nitrogen source) and further containing a saccharide (such as glucose, starch, fructose, etc.) as a carbon source and an inorganic salt or salts (such as phosphate, magnesium salt, etc.) are suited for use in cultivation of Basidiomycetes. However, when a fungus of Basidiomycetes is subjected to submerged culture by using such an aqueous liquid medium, foaming occurs heavily at the surface of the liquid medium during cultivation and hence it proves extremely difficult to carry out cultivation efficiently and smoothly for a large quantity of medium in a fermentor. Therefore, when employing submerged culture of a fungus of the Basidiomycetes by using an aqueous liquid medium prone to foaming as described above, it is necessary to reduce the feed of the medium in the fermentor (to a level of approximately 40 to 60% of the capacity of the fermentor). However, since a considerable number of days are usually required for cultivation of the Basidiomycetes, such reduction of the medium feed leads to lowering of productivity.

Various devices have been employed, such as mounting a defoaming machine to the agitator in the fermentor, for controlling the foaming, but all of these devices are unsatisfactory in suppressing the foaming phenomenon of the medium to such an extent as makes it possible to increase the feed of the medium. It was also attempted to control foaming by reducing the rates of aeration and agitation in the medium, but this method is also undesirable as it lowers the rate of growth of the mycelia of the Basidiomycetes. It was further proposed to dilute the liquid medium to thereby suppress foaming and increase the medium charge, but this attempt is attended with the drawback that the yield of the mycelia per batch is intolerably reduced.

BRIEF SUMMARY OF THE INVENTION

Based upon our study of the phenomenon of foaming which takes place during cultivation of the Basidiomycetes by using an aqueous liquid medium such as described above; we have discovered that although foaming occurs heavily in the initial stage of cultivation, it decreases rapidly when the progress of cultivation reaches a certain stage, and hence if the medium or at least one part of the nutrient source is supplied incrementally in proper portions at the points when the foaming phenomenon decreases in the course of cultivation of the Basidiomycetes, the mycelia can be obtained in a surprisingly high yield.

Accordingly, the primary object of this invention is to provide a novel cultivation method which, when applied to submerged culture of the Basidiomycetes by using an aqueous liquid medium prone to vigorous foaming during cultivation, is capable of producing the mycelia while controlling the foaming phenomenon to allow smooth progress of the cultivation. The other objects of this invention will become apparent from a review of the following detailed description of the invention.

The salient feature of this invention resides in the fact that the aqueous liquid medium used for cultivation of the Basidiomycetes is not fed all at once into the fermentor as in the conventional method, but it is initially fed in an amount of about 70% of the capacity of the fermentor used and then, upon reaching the point in cultivation where the foaming phenomenon decreases, the medium or at least one component of the nutrient source is additionally supplied.

DETAILED DESCRIPTION OF THE INVENTION

In the present invention, the initial charge of the medium, although somewhat varying depending on the composition of the medium used, the size and structure of the fermentor, the agitating rate during cultivation and other factors, is usually within the range of about 40 to 70% of the internal capacity of the fermentor used.

The timing and amount of each additional charge of the medium or at least one component of the nutrient source during the period of cultivation is suitably determined by inspecting the amount of foaming in the medium through an inspection window provided at the top of the fermentor. It is recommended to add an additional charge of the medium or at least one component thereof at any point when the foaming phenomenon has decreased to a certain degree. Such additional charges of the medium or at least one component thereof may be effected either batchwise or continuously while observing the foaming condition. Such supplemental charging operations may increase the total feed of the medium up to about 85% of the capacity of the fermentor.

In cultivation of the Basidiomycetes, not much progress in the growth of the mycelia is observed in the early stage of cultivation and the amount of nutrients in the medium consumed by the Basidiomycetes is limited, so that there takes place little change in the composition of the medium while vigorous foaming phenomenon occurs during the initial phase of cultivation, but it was found that thereafter a rapid decrease of the foaming phenomenon takes place with quick growth of the Basidiomycetes. Therefore, even if the medium feed is controlled to stay less than about 70% of the fermentor capacity during the initial stage of cultivation when violent foaming occurs, the final yield of the mycelia is improved as a sufficient supply of medium or at least one component thereof is given by the additional charges in the last stage of cultivation when the growth of the Basidiomycetes becomes high-paced. In case of using the medium for additional charges, it is preferable to adjust the initial charge such that it is less than about 60% of the capacity of the fermentor used.

The aqueous liquid medium used in this invention contains a saccharide such as glucose, lactose, starch, etc., as a carbon source and at least one member selected from the group consisting of yeast extract, peptone, casamino acid and meat extract as a nutrient source, and preferably, such nutrient source is contained in an amount of more than 0.1 weight %. Such an aqueous liquid medium is prone, when used for submerged culture of the Basidiomycetes, to vigorous foaming at the surface of the liquid medium. The terminology "component(s) of medium" as used to refer to increments added to the medium in accordance with advancement of cultivation has reference to the nutrient source, that is, at least one substance selected from yeast extract, peptone, casamino acid and meat extract.

The method of this invention can be applied for cultivation of a wide variety of fungi belonging to Family Polyporaceae, and it can be advantageously used particularly for cultivation of the Basidiomycetes belonging to the genus Coriolus, particularly those belonging to the species such as *Coriolus versicolor* (Fr.) Quél., *Coriolus consors* (Berk.) Imaz., *Coriolus hirsutus* (Fr.) Quél., *Coriolus pargamenus* (Fr.) Pat., *Coriolus pubesens* (Fr.) Quél. and *Coriolus conchifer* (Schw.) Pat. All of these fungi of Basidiomycetes used in this invention are known in the art, and their mycological properties are given, in "COLORED ILLUSTRATIONS OF FUNGI OF JAPAN" by Rokuya Imazeki and Tsuguo Hongo, Vols. I, 1974, and II, 1975.

According to the method of this invention, even when using an aqueous liquid medium which, which employed for ordinary submerged culture, causes a vigorous foaming phenomenon, the desired submerged culture of the Basidiomycetes when using such a medium can be accomplished smoothly without being affected by the foaming phenomenon, so that it is possible to obtain the mycelia of the Basidiomycetes in a high yield with a reduced number of days for cultivation.

It is to be also noted that polysaccharide is produced as a principal culture product both the obtained mycelia of the Basidiomycetes and in the medium. Such a polysaccharide has various pharmacodynamic effects and also many uses as additives in food processing. Particularly, when using the species listed above as the Basidiomycetes, there can be obtained a polysaccharide having excellent anti-tumor activity. Such a polysaccharide can be separated and recovered by extracting the mycelia obtained from cultivation of this invention and the fermented medium with an aqueous solvent.

EXAMPLE 1

1000 liters of an aqueous liquid medium containing 10 weight % of glucose, 1.5 weight % of yeast extract, 0.2 weight % of malt extract, 0.1 weight % of $MgSO_4 \cdot 7H_2O$ and 0.1 weight % of $KH_2PO_4$ was charged into a vertical tank-shaped fermentor (manufactured by Marubishi Physicochemical Industry Co., Ltd.) having a capacity of 2 $m^3$ and two stages of flat-vaned turbines. After sterilization according to a known method, the medium was inoculated with 20 liters of a slurry of mycelia of *Coriolus versicolor* (Fr.) Quél. previously cultured as seed culture in a 50-liter jar fermentor, and then cultivation was immediately started at an aeration rate of 500 l/min (0.5 l of air supply per liter of medium per minute, that is, 0.5 l/l/min.), a turbine speed of 150 r.p.m. and a cultivation temperature of 26° C. Foam was produced and rose to the top of the fermentor in the initial stage of cultivation, but began to decrease after 15 to 20 hours. So, at the 24th hour from the start of cultivation, 200 liters of the sterilized medium of the same composition as mentioned above was additionally supplied over a period of one hour and cultivation was continued while adjusting the aeration rate to 600 l/min. Foam was again observed rising, but because it decreased with passage of time, 200 liters of medium was again supplied under the same conditions as the first additional charge at the 48th hour from start of cultivation, further continuing cultivation by adjusting the aeration rate to 700 l/min. Foam rose for the third time but here again decreased with time, so at the 72nd hour from start of cultivation, 200 liters of medium was supplied under the same conditions as the first and second additions, with cultivation being further continued by adjusting the aeration rate to 800 l/min. These three supplementations of medium made the total amount of medium supplied 1,600 liters, or 80% of the fermentor capacity, which was almost the maximum amount of feed, so cultivation was continued under these conditions and completed at the 7th day from the start of cultivation. Upon completion of cultivation, the mycelia were centrifugally separated from the medium and dried. The yield was 15.6 g/l.

EXAMPLE 2

1000 liters of an aqueous liquid medium containing 15 weight % of glucose, 2.25 weight % of yeast extract, 0.2 weight % of malt extract, 0.1 weight % of $MgSO_4 \cdot 7H_2O$ and 0.1 weight % of $KH_2PO_4$ was charged into a 2 $m^3$-capacity vertical tank-shaped fermentor having two-staged flat vaned turbines (Mfd. by Marubishi Physicochemical Ind.), and after sterilization according to a known method, the medium was inoculated with 20 liters of a slurry of mycelia of *Coriolus versicolor* (Fr.) Quél. previously cultured as seed culture in a 50-liter jar fermentor. This was immediately followed by the start of cultivation at an aeration rate of 500 l/min (0.5 l of air supply per liter of medium per minute, that is, 0.5 l/l/min), a turbine speed of 150 r.p.m. and a cultivation temperature of 26° C. Foam rose to the top of the fermentor during the early phase of cultivation but began to decrease with the passage of 30 to 40 hours, so at the 48th hour from the start of cultivation, 200 liters of sterilized medium of the same composition as the initially charged medium was additionally supplied over the period of about one hour, and cultivation was continued by adjusting the aeration rate to 600 l/min. Foam was again observed rising but decreased with lapse of time, so at 72nd hour, 200 liters of medium was again supplied under the same conditions as the first additional charge, and cultivation was further continued by adjusting the aeration rate to 700 l/min. Foam was seen rising for the third time but here again decreased with time, so at the 96th hour from start of cultivation, 200 liters of medium was again supplied under the same conditions as the preceding first and second additions and the aeration rate was adjusted to 800 l/min. These three additions brought the total amount of medium supplied to 1,600 liters, or 80% of the fermentor capacity. Because this was close to the maximum amount of feed suppliable, cultivation was continued with no additional supply of medium and ended at the 7th day from start of the cultivation. After completion of cultivation, the mycelia were separated centrifugally from the medium and dried, giving a total yield of 18.4 g/l.

The following tests were also made by way of comparison.

COMPARATIVE EXAMPLE 1

1,200 liters of medium of the same composition as that of Example 1 was fed all at once into a tank-shaped fermentor same as used in Example 1, and after sterilization according to an ordinary method, the medium was inoculated with 20 liters of slurry of mycelia of *Coriolus versicolor* (Fr.) Quél. previously cultured as seed culture in a 50-liter jar fermentor, immediately followed by start of cultivation at an aeration rate of 500 l/min, a turbine speed of 150 r.p.m. and a cultivation temperature of 26° C. The cultivation was continued for 7 days.

The yield of the mycelia obtained in the same way as Example 1 after completion of cultivation was 16.9 g/l.

The obtained result shows that the yield of mycelia per unit amount of medium is rather higher in Comparative Example 1 than in Example 1, but in the former it was impossible to feed the medium in an amount of more than 60% of the fermentor capacity owing to excessive foaming in the medium, so that the production of mycelia per batch was lower than Example 1, as shown in Table 1 below.

COMPARATIVE EXAMPLE 2

Cultivation was carried out by following the same procedure as Comparative Example 1 except that a feed of 1,000 liters of medium of the same composition as that of Example 2 was introduced as a single charge. It was practically impossible to feed more than 1,000 liters of medium owing to excessive foaming in the medium. Results are shown in Table 1.

COMPARATIVE EXAMPLE 3

Cultivation was performed according to the same procedure as Comparative Example 1 except for feeding a single charge of 1,600 liters of medium containing 5 weight % of glucose, 0.75 weight % of yeast extract, 0.2 weight % of malt extract, 0.1 weight % of $MgSO_4.7H_2O$ and 0.1 weight % of $KH_2PO_4$. In this case, the amount of medium feed was equalized to the total feed in Examples 1 and 2 by diluting the medium used. That is, the foaming phenomenon was decreased by using the diluted medium. The obtained results were as shown in Table 1.

tute, Agency of Industrial Science and Technology, Chiba, Japan, under deposit number of FERM-P No. 2412 on Dec. 25, 1973 and is also disclosed in the specification of U.S. Ser. No. 755,142, filed on Dec. 29, 1976). The mycelia slurry was obtained from a shaking culture, and cultivation was immediately started at an aeration rate of 0.5 l/l/min, a speed of 250 r.p.m. and a cultivation temperature of 25°±2° C. Foam rose to the top of the fermentor during the initial stage of cultivation but began to decrease after 15 to 20 hours, so at a point 24 hours after start of cultivation, 2 liters of an aqueous solution containing yeast extract was supplied additionally and cultivation was continued by adjusting the aeration rate to 0.6 l/l/min. Foams again rose but decreased with passage of time, so at a point 48 hours after start of cultivation, 2 liters of the aqueous solution was again added, continuing cultivation by adjusting the aeration rate to 0.6 l/l/min. Likewise, 2 liters of the aqueous solution was once again additionally supplied at a point 72 hours after start of cultivation and cultivation was further continued.

These three additions of the aqueous solution plus the initial charge made the total feed of medium 41 liters, or 82% of the fermentor capacity. As this was almost the maximum amount of feed, cultivation was continued with this amount of medium and ended at 7th day from start of cultivation.

After completion of cultivation, the mycelia were centrifugally separated from the medium and dried. The yield and production were 19.8 g/l and 810 g, respectively, as shown in Table 2 below.

By way of comparison, the mycelia of Coriolus versic-

TABLE 1

|  | Example 1 | Example 2 | Comp. Example 1 | Comp. Example 2 | Comp. Example 3 |
|---|---|---|---|---|---|
| Medium composition (wt %) |  |  |  |  |  |
| Glucose | 10 | 15 | 10 | 15 | 5 |
| Yeast extract | 1.5 | 2.25 | 1.5 | 2.25 | 0.75 |
| Malt extract | 0.2 | 0.2 | 0.2 | 0.2 | 0.2 |
| Mg $SO_4$ . $7H_2O$ | 0.1 | 0.1 | 0.1 | 0.1 | 0.1 |
| $KH_2PO_4$ | 0.1 | 0.1 | 0.1 | 0.1 | 0.1 |
| Final feed rate (%) | 80 | 80 | 60 | 50 | 80 |
| Total feed (l) | 1600 | 1600 | 1200 | 1000 | 1600 |
| Production of mycelia (kg/batch) | 24.96 | 29.44 | 20.28 | 20.90 | 17.76 |

(Note):
Cultivation was performed for 7 days in all cases.

EXAMPLE 3

In this example, a component used as a nutrient source in the medium was used for the supplemental charge instead of the medium itself.

35 liters of the liquid medium containing glucose and yeast extract as shown in Table 1 was fed into a 50-liter vertical tank-type flat vaned fermentor, and after sterilization according to an ordinary method, the medium mixture was inoculated with a slurry of mycelia (0.01% measured as mycelia) of Coriolus versicolor (Fr.) Quél. CM-101 (deposited at the Fermentation Research Instiolor (Fr.) Quél. were cultivated in the same fermentor as used in Example 3 with no additional supply of yeast extract to the aqueous liquid medium blended with a relatively large amount of yeast extract as compared with glucose as shown in Table 2. In this case, it was impossible to feed more than 25 liters of medium due to excessive foaming. The yield of mycelia after a 7-day cultivation was 22.0 g/l and the production was 550 gr.

These results reveal the fact that the method of this invention is capable of significantly increasing the production of mycelia in a given fermentor.

TABLE 2

|  | Present invention | | Comparative Example | |
|---|---|---|---|---|
| Initial charge of medium | 35 l | { Glucose content 3000 g<br>Yeast extract cont. 200 g | 25 l | { Glucose cont. 1875 g<br>Yeast extract cont. 375 g |
| Additional charges of solution containing yeast extract |  | First (24 hrs later) 2 l<br>(yeast extract cont. 100 g)<br>Second (48 hrs later) 2 l<br>(yeast extract cont. 100 g)<br>Third (72 hrs later) 2 l |  |  |

TABLE 2-continued

|  |  | Present invention | Comparative Example |
|---|---|---|---|
|  |  | (yeast extract cont. 100 g) |  |
| Total amount of medium fed |  | 41 liters | 25 liters |
| Cultivation conditions | Time | 7 days | 7 days |
|  | Temperature | 25 ± 2° C. | 25 ± 2° C. |
| Mycelia | Production | 810 g | 550 g |

(Note):
In the above table, the glucose concentration in the medium charged was 7.5% in both cases, and the yeast extract concentration (total of the additional charges in the present invention and that in the initial medium charge in the comparative example) was 1.5%.

EXAMPLE 4

Mycelia of *Coriolus versicolor* (Fr.) Quel. CM-101 were cultivated by the same procedure in a 50-liter fermentor as was used in Example 1. 30 liters of a medium composed of glucose and yeast extract as shown in Table 3 was initially charged and inoculated with the *Coriolus mycelia* slurry. At the 48th hour and the 72nd hour from start of cultivation, 5 liters of yeast extract was additionally supplied and cultivation of the mycelia was further continued. The results are shown in Table 3.

For comparison, a similar cultivation was performed by using a medium blended with a large amount of yeast extract relative to glucose without adding any additional supply of yeast extract to the medium. In this case, foaming occured heavily as in the case of the comparative example for Example 3 and this made it impossible to feed more than 20 liters of the medium. Accordingly, the production of the mycelia was low as shown in Table 3 below.

TABLE 3

|  | Present invention |  | Comparative Example |  |
|---|---|---|---|---|
| Initial charge of medium | 30 l | Glucose content 4000 g<br>Yeast extract cont. 400 g | 20 l | Glucose cont. 2000 g<br>Yeast extract cont. 350 g |
| Additional charge of solution containing yeast extract |  | First (48 hrs. later) 5 l<br>(yeast extract cont. 200 g)<br>Second (72 hrs. later) 5 l<br>(yeast extract cont. 100 g) |  |  |
| Total feed of medium |  | 40 l |  | 20 l |
| Cultivation conditions | Time | 7 days |  | 7 days |
|  | Temperature | 26° C. |  | 26° C. |
| Mycelia | Production | 1110 g |  | 616 g |

What is claimed is:

1. In the method of cultivating a Basidiomycetes fungus in a fermentor under aeration and agitation at a temperature of 25°±2° C. by using an aqueous culture medium containing a saccharide as a carbon source and at least one nutrient source selected from the group consisting of yeast extract, peptone, casamino acid and meat extract and being prone to foaming in the initial stage of cultivation, the improvement wherein the initial charge of said culture medium is less than about 70% of the capacity of the fermentor, initially allowing said culture medium in the fermentor to foam and adding additional charges of said culture medium or a nutrient component selected from the group consisting of yeast extract, peptone, casamino acid and meat extract until at least about eighty-five percent of the fermentor's capacity is occupied by the aqueous culture medium with the proviso that each additional charge is supplied at a point in the course of cultivation when said foaming has subsided.

2. The cultivation method according to claim 1, wherein said Basidiomycetes is a fungus belonging to Polyporaceae.

3. The cultivation method according to claim 2, wherein said fungus belonging to Polyporaceae is a fungus belonging to the genus Coriolus.

4. The cultivation method according to claim 3, wherein said fungus belonging to the genus Coriolus is *Coriolus versicolor* (Fr.). Quel.

5. The cultivation method according to claim 1, wherein said initial charge of the medium is less than about 60% of the capacity of the fermentor.

6. The cultivation method of claim 1, wherein additional charges of said nutrient component are added batchwise.

7. The cultivation method of claim 1, wherein additional charges of said nutrient component are added in a continuous fashion.

* * * * *